(12) United States Patent
Luo et al.

(10) Patent No.: US 12,186,022 B2
(45) Date of Patent: Jan. 7, 2025

(54) DEVICE AND SYSTEM FOR MULTIDIMENSIONAL DATA VISUALIZATION AND INTERACTION IN AN AUGMENTED REALITY VIRTUAL REALITY OR MIXED REALITY IMAGE GUIDED SURGERY

(71) Applicant: ImmersiveTouch, Inc., Chicago, IL (US)

(72) Inventors: Jia Luo, Chicago, IL (US); Jonathan Linsner, Chicago, IL (US); P. Pat Banerjee, Chicago, IL (US); Christopher Orris, Chicago, IL (US); Jay Banerjee, Chicago, IL (US)

(73) Assignee: ImmersiveTouch, Inc., Chicago, IL (US)

( * ) Notice: Subject to any disclaimer, the term of this patent is extended or adjusted under 35 U.S.C. 154(b) by 213 days.

(21) Appl. No.: 18/048,681

(22) Filed: Oct. 21, 2022

(65) Prior Publication Data
US 2023/0054394 A1 Feb. 23, 2023

Related U.S. Application Data

(63) Continuation-in-part of application No. 17/859,655, filed on Jul. 7, 2022, which is a continuation-in-part
(Continued)

(51) Int. Cl.
*G06T 19/20* (2011.01)
*A61B 34/00* (2016.01)
(Continued)

(52) U.S. Cl.
CPC .............. *A61B 34/10* (2016.02); *A61B 34/20* (2016.02); *A61B 34/25* (2016.02); *A61B 34/76* (2016.02); *A61B 90/361* (2016.02); *A61B 90/50* (2016.02); *G06F 3/011* (2013.01); *G06T 19/006* (2013.01); *G06T 19/20* (2013.01); *A61B 2034/102* (2016.02); *A61B 2034/105* (2016.02); *A61B 2034/2055* (2016.02);
(Continued)

(58) Field of Classification Search
None
See application file for complete search history.

(56) References Cited

U.S. PATENT DOCUMENTS

2008/0101667 A1 5/2008 Begelman et al.
2013/0278631 A1* 10/2013 Border ................ G06F 3/04842
345/633
(Continued)

OTHER PUBLICATIONS

Ziegler, G., et al., "On-the-fly Point Clouds through Histogram Pyramids", Computer Graphics Stuhlsatzenhausweg 85, pp. 1-9.
(Continued)

*Primary Examiner* — Robert J Craddock
(74) *Attorney, Agent, or Firm* — DLA Piper LLP (US)

(57) ABSTRACT

The present technology relates to devices and systems for multidimensional data visualization and interaction in an augmented reality, virtual reality, or mixed reality image guided surgery. The disclosed embodiment provides a tool for a physician or other medical specialist to load and review
(Continued)

medical scans in an AR/VR/MR environment, assisting medical diagnostics, surgical planning, medical education, or patient engagement.

11 Claims, 7 Drawing Sheets

Related U.S. Application Data of application No. 17/126,570, filed on Dec. 18, 2020, now Pat. No. 11,416,069, which is a continuation-in-part of application No. 16/839,803, filed on Apr. 3, 2020, now Pat. No. 10,872,460, which is a continuation-in-part of application No. 16/138,209, filed on Sep. 21, 2018, now Pat. No. 10,650,604.

(51) Int. Cl.
| | | |
|---|---|---|
| A61B 34/10 | (2016.01) | |
| A61B 34/20 | (2016.01) | |
| A61B 90/00 | (2016.01) | |
| A61B 90/50 | (2016.01) | |
| G06F 3/01 | (2006.01) | |
| G06T 19/00 | (2011.01) | |

(52) U.S. Cl.
CPC . *A61B 2034/2065* (2016.02); *A61B 2090/365* (2016.02); *A61B 2090/3983* (2016.02); *A61B 2090/502* (2016.02); *G06T 2210/41* (2013.01); *G06T 2219/2021* (2013.01)

(56) References Cited

U.S. PATENT DOCUMENTS

| | | |
|---|---|---|
| 2014/0063054 A1 | 3/2014 | Osterhout et al. |
| 2014/0088941 A1 | 3/2014 | Banerjee et al. |
| 2016/0092645 A1 | 3/2016 | Vlutters et al. |
| 2017/0108930 A1 | 4/2017 | Banerjee et al. |
| 2019/0026935 A1 | 1/2019 | Podziemski et al. |

OTHER PUBLICATIONS

Frieder, G., et al., "Back-to-Front Display of Voxel-Based Objects", pp. 1-9, IEEE (1985).
Pfister, H., et al., "Hardware-Accelerated Volume Rendering", pp. 1-16, The Visualization Handbook, (2005).
Volumetric Sort, Inigo Quilez, URL, http://iquilezles.org/www/articles/volumesort/volumesort.htm, downloaded on Mar. 28, 2019, p. 1.
Vega-Higuera, F., et al., "High Performance vol. Splatting for Visualization of Neurovascular Data", pp. 271-278, IEEE Visualization (2005).
Orchard, J., et al., "Accelerated Splatting using a 3D Adjacency Data Structure", School of Computing Science, p. 10, (2001).
Co-Pending U.S. Appl. No. 17/859,655, downloaded on Nov. 18, 2024.

\* cited by examiner

DEVICE AND SYSTEM FOR MULTIDIMENSIONAL DATA VISUALIZATION AND INTERACTION IN AN AUGMENTED REALITY VIRTUAL REALITY OR MIXED REALITY IMAGE GUIDED SURGERY

CROSS-REFERENCE TO RELATED APPLICATIONS

This is a continuation in-part of U.S. patent application Ser. No. 17/859,655, filed Jul. 7, 2022, which is a continuation-in-part of U.S. patent application Ser. No. 17/126,570 filed Dec. 18, 2020, which is a continuation-in-part of U.S. patent application Ser. No. 16/839,803 filed Apr. 3, 2020, now U.S. Pat. No. 10,872,460, which is a continuation-in-part of U.S. patent application Ser. No. 16/138,209 filed Sep. 21, 2018, now U.S. Pat. No. 10,650,604. The above-mentioned applications and patents are incorporated herein by reference in their entirety.

FIELD OF THE INVENTION

The present technology relates to devices and systems for multidimensional data visualization and interaction in an augmented reality, virtual reality, or mixed reality environment.

BACKGROUND

Augmented reality (AR), virtual reality (VR), and mixed reality (MR) are immersive technologies that provide innovative and powerful ways for people to create, perceive, and interact with information in digital forms.

VR technology takes traditional media such as, but not limited to, a photographic image, a video, a sound, and a computer-generated graphics, beyond conventional two-dimensional (2D) screens, and presents them with a three-dimensional (3D), immersive and real-time interactive experience. The AR and MR technologies further enhance a user's perceptions of reality by aligning the physical world with the virtual digital media. AR/VR/MR are emerging technologies and can be used in business, entertainment, research, education, data visualization and other fields yet to be imagined.

Healthcare is one of the most popular use cases for AR/VR/MR technologies. There is a clear need and desire for a tool in healthcare that helps in visualizing and interacting with medical information such as, but not limited to, patient anatomies in real-world environment through AR/VR/MR technologies. The tool would be useful from medical diagnostic platforms to surgical planning solutions using high resolution scanned image data such as a magnetic resonance imaging (MRI) scan, a computer tomography (CT) scan, a digital radiography (DR) scan, or an ultrasound scan. Such a tool would also help in the better visualization of the anatomical structures and therefore, can be used for training of residents and medical students, or patient engagement and education.

BRIEF DESCRIPTION OF THE DRAWINGS

Specific examples have been chosen for purposes of illustration and description, and are shown in the accompanying drawings, forming a part of the specification.

DETAILED DESCRIPTION

Figure 1:
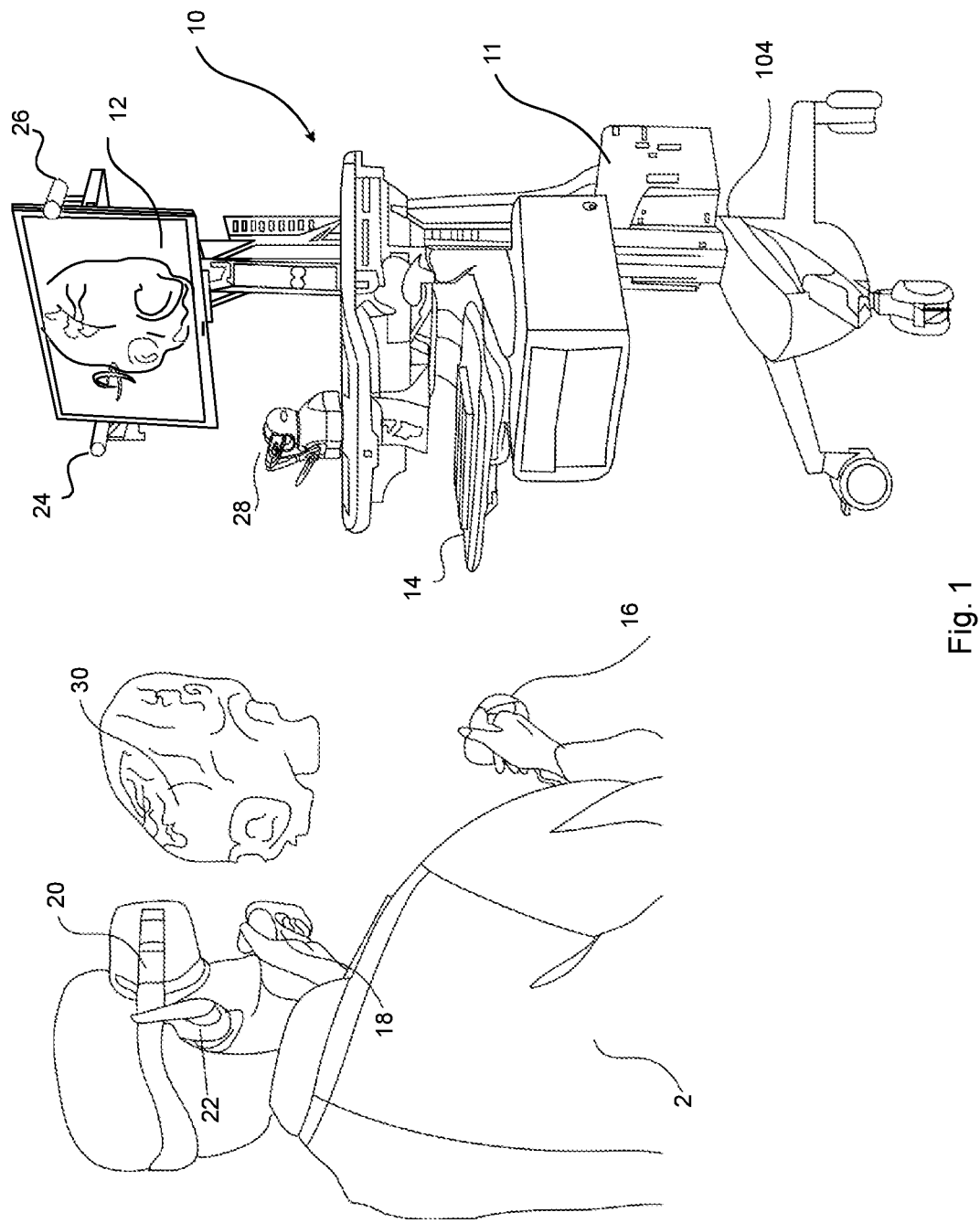
FIG. 1 illustrates one example of a portable workstation in accordance with the disclosed technology.

The presented technology relates to devices and systems for multidimensional data visualization and interaction in an augmented reality, virtual reality, or mixed reality environment. The disclosed embodiments generally apply to volumes of all sources, including but not limited to a medical imaging, an industrial computed tomography scanning, a three-dimensional (3D) or two-dimensional (2D) mathematical modeling, 3D or 2D scientific dataset, and the like. In a medical environment, the disclosed embodiments provide a tool for a doctor, physician, or other medical technician to quickly load and review patient scans in an AR/VR/MR environment. Moreover, unique, and unobstructed views of the patient's scans are easily obtainable. The physician or technician may manage a scan as if it were a physical object in a palm of his/her hand, observing it from any angle to get the best understanding of the situation at any zoom and detail level desired.

In an augmented reality configuration, the presented technology allows a user to see computer-generated 3D images overlaid in the real world, positioned correctly in relation to real objects of significance, such as parts of a patient's body or a surgeon's tools. Often, but not always, the rendered objects are identical to these features and are placed exactly where the real features are, so that the rendered versions are visible when the real objects are occluded, usually by skin or other anatomy. In a desired embodiment, the augmented reality applications of the presented technology have particular value for minimally invasive surgeries where almost the entire surgery happens underneath the patient's skin without direct visibility. Rendered images may also be purely informational. For example, it may highlight a line around a bone exactly where it needs to be cut, or draw a line along the vector through which a surgical instrument must be inserted.

In a medical environment the disclosed embodiments generally apply to the presentation of one or multiple 3D medical imaging scans of a plurality of modalities, including but not limited to a computed tomography (CT) technique, a magnetic resonance imaging (MRI) technique, a CT angiography (CTA) technique, a MR angiography (MRA) technique, a Cone Beam CT (CBCT) technique, etc., and their post processing results. The CT technique may be a computerized x-ray imaging procedure that produces signals processed by computer to generate cross-sectional images of the body. The MRI technique may be a non-invasive imaging procedure that uses strong magnetic fields, magnetic field gradients and radio waves to produce 3D detailed anatomical images. The CTA technique may be a procedure that applies the CT technique on a patient with an injection of a special dye to produce pictures of blood vessels and tissues in the body. The MRA technique may be a technique based on the MRI technique and the injection of contrast agents for studying arterial and venous systems. The CBCT technique may be a variant of the computed tomography (CT), and is used particularly in dental and extremity imaging.

In a medical environment, the disclosed embodiments further apply to one or multiple medical imaging scans with other multidimensional data, including but not limited to a digital radiography (DR) technique, an ultrasonography technique, and their post processing results. The DR technique may be a procedure that utilize a wide beam of x-rays for 2D image acquisition of a patient. The ultrasonography technique may be a procedure that uses high frequency broadband sound waves that may be reflected by anatomy tissue to produce images of internal structures of the body.

In a medical environment, the disclosed embodiments may apply to all medical specialties that utilize the medical imaging, including but not limited to radiology, orthopedic surgery, craniomaxillofacial surgery, dentistry, cardiothoracic surgery, neurosurgery, neurology, spine surgery, otorhinolaryngology, general surgery, internal medicine, etc.

The disclosed embodiments utilize geometric primitives referred to herein as "voxels", arranged in a "volume". It should be appreciated that the precise appearance or mathematical definition of the voxels varies by application and is not essential to practice the embodiments disclosed herein. These geometric primitives include that: each primitive may be uniquely identified by 3 integral coordinates (x, y, z); the (x, y, z) values of the primitives' integral coordinates have a finite range; each primitive may be geometrically contained within a pyramid with a regular cuboidal bounding extent; the regular cuboidal bounding extents of no two primitives intersect in three dimensions; and the (x, y, z) lengths of the regular cuboidal bounding extents do not differ between any two primitives.

Figure 2:
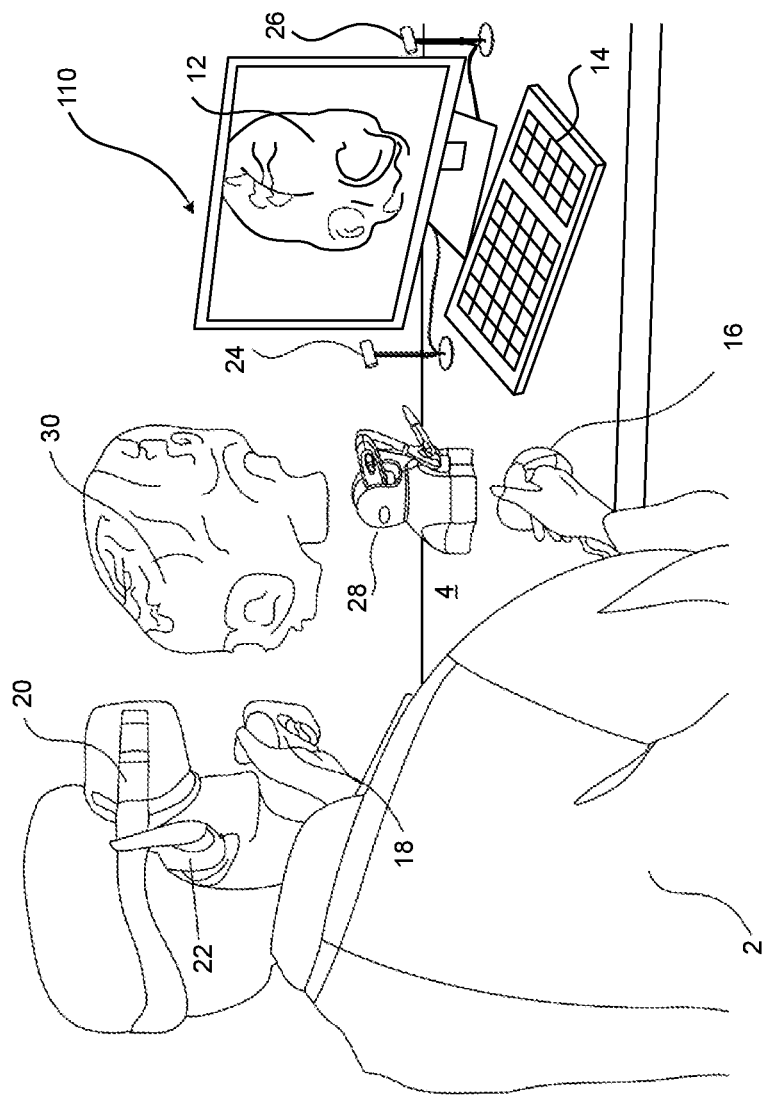
FIG. 2 illustrates one example of a workstation in accordance with the disclosed technology.
Figure 3:
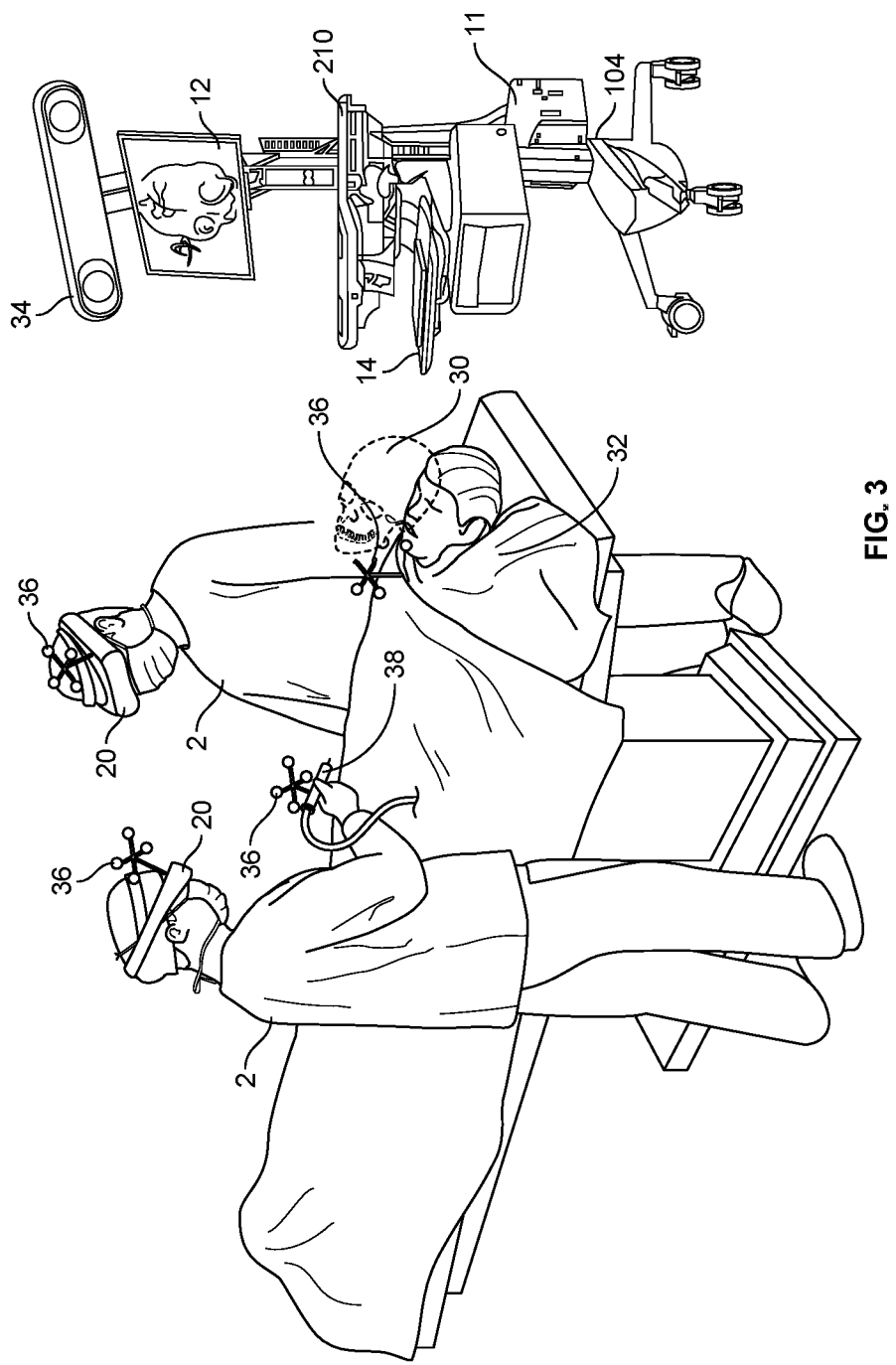
FIG. 3 illustrates one example of a multi-user AR workstation in accordance with the disclosed technology.

FIG. 1 illustrates one example of a portable workstation 10 in accordance with the disclosed technology; FIG. 2 illustrates one example of a workstation 110 in accordance with the disclosed technology while FIG. 3 illustrates one example of a workstation 210 with an Augmented Reality configuration of the disclosed technology. In the illustrated examples, the workstations 10, 110 and 210 may include one or more AR/VR/MR devices and/or one or more haptic devices, which along with the data visualization and interaction discussed herein provide several advantages previously unattainable in the art. In one or more embodiments, the workstations may not include the haptic device. Thus, the disclosed principles and advantages over the current state of the art are obtainable on workstations 10, 110 and 210 that may not have the one or more haptic devices.

Referring to FIG. 1, the workstation 10 includes a computer 11, a display screen 12, a set of keyboard and mouse 14. The workstation 10 is shown being provided on a compact wheeled carrier 104, making the workstation 10 easily transportable. The workstation 10 is shown being operated by a user 2. In the illustrated example, the user 2 is wearing an AR/VR headset 20 for viewing a stereoscopic visualization 30 of one or more sets of 3D volume data or 2D image data input into the workstation 10 and rendered by the workstation 10 in accordance with the disclosed principles. In the illustrated embodiment, a rendering of one or more 3D volume datasets or 2D image datasets in accordance with the disclosed principles may also be presented on the display screen 12.

The AR/VR headset 20 helps in viewing one or more anatomical structures by the visualization 30 of one or more sets of 3D volume data or 2D image data. The visualization 30 may be in 2D or in 3D and may be viewed from different angles and positions. The visualization 30 of one or more anatomical structures may be projected onto the actual patient which the data was previously scanned from. The visualization 30 may be superimposed with the corresponding actual anatomical structures by collocating the 3D volume data or the 2D image data with the patient body.

The AR/VR headset 20 may be connected to the workstations 10, 110 for receiving and conveying the data. Said connection may be achieved by one or more universal serial bus (USB) or display cables. The connection may also be established network connections between the workstations 10, 110 and the AR/VR headsets 20 which have standalone computation and communication capabilities. The network connection may be a local area network such as Wi-Fi network, or a high speed and low latency wide area network such as 5G cellular network or fiber broadband network.

The user 2 is also shown wearing a headphone 22 for listening to auditory simulations as the user 2 observes and interacts with the volume or the image data input into the workstation 10. In the illustrated example, the user 2 is operating two hand controllers 16, 18 also used to interact with the data rendered by the workstation 10 in accordance with the disclosed principles.

Referring to FIG. 2, the workstation 110 includes a computer (not shown), a display screen 12, a set of keyboard and mouse 14. The workstation 110 is shown being operated by the user 2 at a desk 4 or other workspaces. As explained below in more detail, due to the novel multidimensional data visualization and interaction provided by the disclosed principles, patient-specific data is easily loaded into, rendered, and interacted with in both workstations 10, 110 making the workstations 10, 110 suitable for viewing critical scan information in all areas of health care facilities, including but not limited to a radiology lab, an operating room, an emergency room or a doctor's office. The workstations 10, 110 may also be suitable for patient education and engagement. Patients may be able to better understand their condition and physicians may walk the patients through proposed interventions, actively consulting with them to determine the best therapeutic choice for their respective situations. This may reduce patient anxiety and reinforce the patients understanding of their treatment and increase informed consent for medical plans of action.

Referring to FIG. 3, the workstation 210 includes a computer 11, such as a desktop PC or laptop, an optical tracking device 34 connected to the computer 11 for reporting the positions of real objects of significance, and a network router (not shown) for connecting the computer 11 with one or more AR headsets 20 and other devices as needed, such as the optical tracking device 34. Other input and output devices, such as the display screen 12 and the keyboard and mouse 14 are available for the user 2 to interact with the workstation 210 via graphics user interfaces (GUI).

In an embodiment, the optical tracking device 34 may be a separate equipment that is physically connected with the computer 11. In another embodiment, the optical tracking device 34 may be a software component that receives optical input data from existing optical sensors on the AR headset 20 or any other devices of the workstation 210. The optical marker objects 36 are designed to work with the optical tracking device 34 and they may be of different modalities based on the visual fiducial system used by the optical tracking device 34. In a desired embodiment, the optical marker object 36 may be a constellation of spheres or other geometric primitives, a two-dimensional bar code such as a QR code, a constellation of 2D bar codes, a 2D image, or a 3D object.

The optical marker objects 36 may be attached to one or more real objects of significance and one or more AR headsets 20 to track their real time position and orientation. In the illustrated embodiment, the real objects of significance may be the patient anatomy 32 or one or more surgical instruments 38. Custom attachments are used to connect the markers to objects of significance. In a medical environment, the attachments may be custom-designed, 3D printed objects that attach to a fixture on the patient body, or directly to the patient anatomy 32 which is typically the bone. There may also be such attachments on the AR headsets 20.

The workstation 210 is shown being operated by one or more users 2. In the illustrated example, each user is wearing an AR headset 20, which is a transparent visor with an onboard computer that allows the user to see 3D images overlaid over the real world. The AR headset 20 presents to the user 2 a stereoscopic visualization 30 of one or more 3D objects or 2D images. The optical tracking device 34 reports the position of all the markers that it sees to the workstation 210. The offset between each optical marker object 36 and the object of significance it's attached to is known ahead of time, based on the shape of the attachment. Similarly, the view perspective of the user 2 may be computed based on the tracked position and orientation of the AR headset 20 as well as the offset between the headset and user 2's both eyes. The workstation 210 uses these offsets to draw each rendered object in the correct location from the view perspective of the user 2, allowing the stereoscopic visualization 30 of the 3D objects or 2D images to be superimposed to their real-world counterparts, which may be the patient anatomy 32 or one or more surgical instruments 38.

Figure 4:
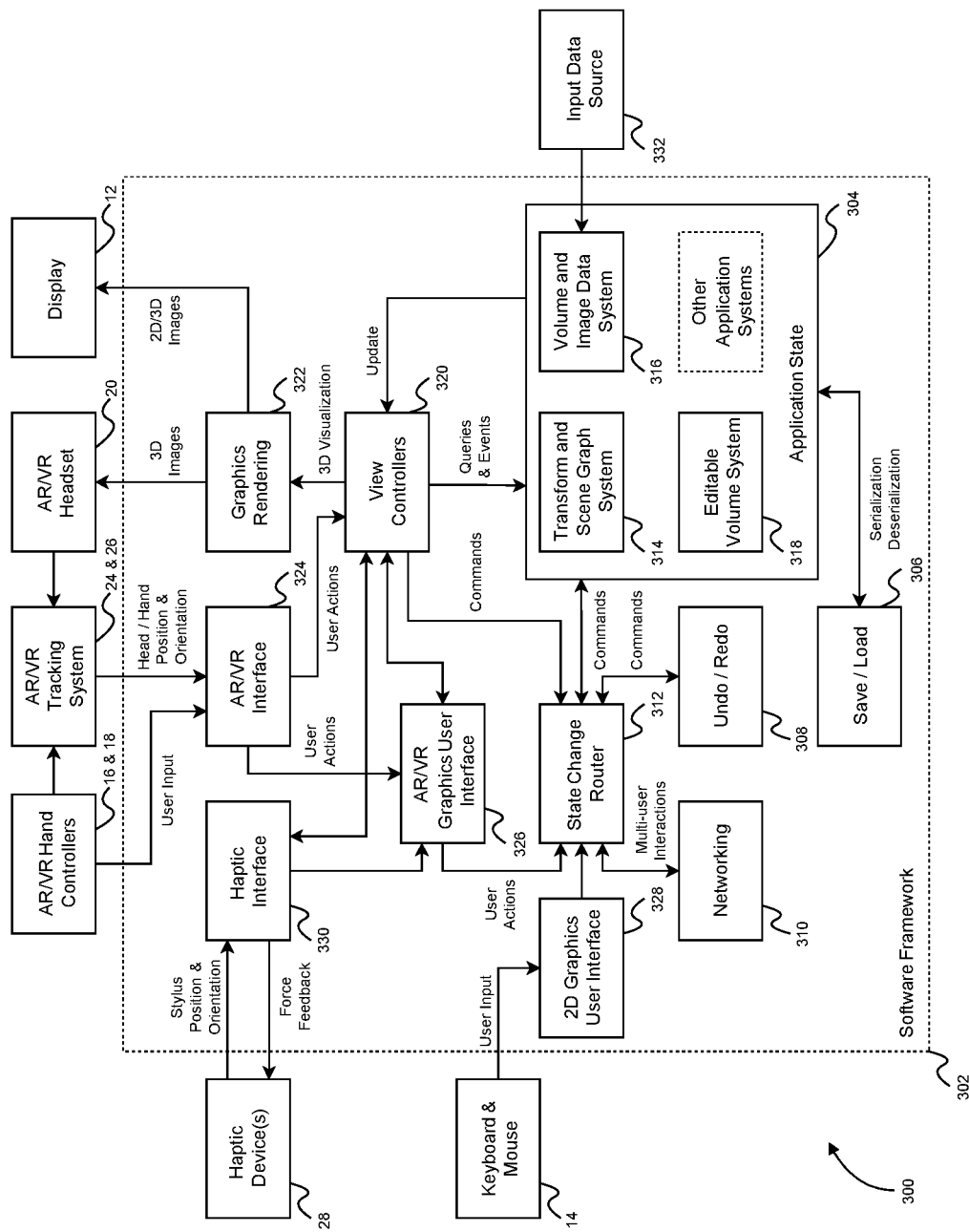
FIG. 4 illustrates a block diagram of a software and hardware architecture for the workstations illustrated in FIGS. 1, 2 and 3.

FIG. 4 illustrates a block diagram of a software and hardware architecture 300 for the workstations illustrated in FIGS. 1, 2 and 3. In the illustrated example, the architecture 300 includes interconnected devices and logic that are integrated by a software framework 302.

The software framework 302 includes an Application State module 304 which maintains one or more virtual scenes. Each virtual scene is a distinct state of the application that contains all data and content presented in AR/VR/MR. The Application State module 304 further comprises one or more application systems and system data. Each application system has corresponding system data, and each system data has a corresponding application system. The Application State 304 maintains all application systems and the system data associated therewith for lifetime of the application. The Application State 304 allows querying and interaction with any of the application system and the system data associated therewith in a specific and controlled manner. Each application system includes logic for creating, modifying, and destroying the corresponding data and serves as a target for all application commands. The application system also includes a public interface that allows querying current events and subscribing to an event that is called whenever the system data is created, modified, or destroyed. The changes made in the data may be preserved even after the user 2 leaves the scene.

The application systems comprised in the Application State module 304 may include a transform and scene graph system 314, a volume and image data system 316, a view object system 318 and plurality of other application systems that define application-specific features and user interactions.

The software framework 302 further comprises a Save/Load module 306 for saving and loading operations. The saving operation serializes all application systems and the system data associated therewith in the Application State 304 of an active session, including one or more original, processed, or edited volume or image data, their surface representation, as well as results of the user interactions, and saves into external files. The loading feature loads complete set of data from a file, deserializes the data and then initializes the Application State 304 as well as all relevant application systems and system data. In a desired embodiment, saved data may be saved in a portfolio of files with a unique file extension, so the loading process can identify the files by such file extension.

The Save/Load module 306 further comprises a feature that converts the surface representation of the original, processed, or edited volume or image data into polygon mesh model files and save them into the file system. In one embodiment, the polygon mesh models may be saved as STL files, OBJ files, or 3MF files.

The software framework 302 includes a State Change Router 312 that serves as a hub of the application commands. Application commands may describe the creation, modification or destruction of the system data corresponding to one or more application systems. Application commands may be received from the user interactions through AR/VR GUI 326 or 2D GUI 328, or from command issuers, which may be the View Controllers 320, the Undo/Redo module 308, or the Networking module 310. Upon receiving the commands, the State Change Router 312 further sends them to command listeners, which may be plurality of application systems in the Application State 304, the Undo/Redo module 308, or the Networking module 310.

The software framework 302 further comprises an Undo/Redo module 308 for undo and redo operations. The Undo/Redo module 308 receives new application commands from the State Change Router 312 and stores the commands in a command stack for undo and redo operations. The undo operation reverses the user interaction and recovers the system data at a previous state; the redo operation reverses an undo operation and recovers the system data at a state prior to the undo operation.

Features and operations in the plurality of application systems are implemented by performing a plurality of low-level operations on the system data. To group low level operations into a single logical high-level operation, all tools perform the operations on a context object which may be first acquired from the State Change Router 312. This also serves as a locking mechanism to prevent multiple tools from modifying the one or more system data in unpredictable ways.

Each low-level operation may be implemented as a command that records the before and after states of its execution. When a tool performs operations, the context records a list of all the commands that have been executed by the current tool. When the tool is finished making changes, it releases the context to finalize its changes. The context bundles the low-level operations into a single high-level undo/redo operation so that when the user 2 triggers the undo feature, all changes made by the last tool will be reverted, even if they consist of multiple sub-commands. Once the high-level undo/redo command is assembled, it is added to a stack of previous undo-redo commands. Operations may be undone and redone by applying the appropriate state from each command. The undo/redo stack can also be serialized and saved to disk, both to support resuming a session, but additionally as a record of all the steps taken in the planning session.

The software framework 302 further comprises a Networking module 310 which supports multi-user interaction and collaboration over the network. The Networking module 310 sends the multi-user interaction data or commands from the State Change Router 312 to other users on a network. The networking module also receives the interaction data from the other users and sends it to the State Change Router 312 to modify the data held by the Application State 304 on behalf of a remote user.

The Networking module 310 may allow multiple users to share and synchronize the entire Application State 304, all application systems and the system data associated therewith, as well as the undo/redo stack, so multiple users may interact with the same volume objects in their own AR/VR/MR environment. Any user may be able to view and interact with one or more volume or image data, and see the changes made by others applied locally. In one embodiment, a voice/chat feature may be provided to allow users to communicate directly. The network connection may be over a local area network or a wide area network such as the Internet.

In the illustrated embodiment, the software framework 302 includes a plurality of View Controllers 320 for visualizing the system data to the user 2 as a plurality of 3D objects, 2D objects, or graphical user interfaces (GUIs) and giving the user means to interact with the 3D/2D objects and their underlying data. The plurality of View Controllers 320 is in place for querying the public interface of the Application State 304 for the state of one or more application systems, subscribing to events that will trigger if the data changes, and issuing the commands to create, modify, or destroy the system data based on the user instruction with plurality of interaction features. The plurality of View Controllers 320 issue the commands through the State Change Router 312. In an embodiment, the plurality of View Controllers 320 may send the command in a direct mode or an indirect mode through the AR/VR GUI 326 to the State Change Router 312.

In the illustrated embodiment, the software framework 302 may include the AR/VR interface 324 for interfacing with the AR/VR hardware, including one or more AR/VR tracking system 24, 26, AR/VR headsets 20 and hand controllers 16, 18 worn or operated by the user 2. The AR/VR interface 324 receives the positions and orientations of user's head or hands, as well as all user inputs from AR/VR hand controllers 16, 18. In a desired embodiment, the AR/VR tracking system 24, 26 may track the pose of user 2's hands and further recognize hand gestures, which may trigger user actions. Said user inputs and actions are used to update the AR/VR GUI 326 and interact with plurality of View Controllers 320.

The software framework 302 further includes the graphics rendering module 322 which renders the visualization of the system data from all application systems as images captured from one or more specific viewpoints. The graphics rendering module 322 receives the system data through the plurality of View Controllers 320 and visualizes the data on one or more 2D planes or in a 3D space via plurality of graphics rendering mechanisms.

The graphics rendering module 322 may provide plurality of camera nodes that compute the correct viewer-centered perspective projection on virtual projection planes. In an embodiment, the graphics rendering module 322 may stereographically render a view of the Application State on the AR/VR headset 20. The rendering perspective may be consistent with a physical position and an orientation of the AR/VR headset 20. The graphics rendering module 322 may properly render both left and right views according to the position and orientation of the user's head given by the AR/VR interface 324. The graphics rendering module 322 is performed by the graphics processing units; the rendering results may be presented on the display screen 12 and the AR/VR headset 20 and may be reproduced on the 2D GUI 328 or the AR/VR GUI 326, which may be presented on the display screen 12 and the AR/VR headset 20.

The graphics rendering module 322 further includes a remote rendering technique which uses the computer 11 of the workstation 210 to render the images based on the view perspective of the AR/VR headset 20, and send them to the headset to draw in front of the user's eyes. With a more powerful graphics processing unit and larger memory, the remote rendering technique may provide images of far greater 3D resolution and visual fidelity than is typically possible with modern standalone AR/VR headsets, which have limited computational power onboard (roughly equivalent of a modern cell phone).

A common challenge in all applications of remote rendering is the latency between a user performing an action and having it represented in the images. In the case of the presented technology, the displayed image is dependent on the position and orientation of the user's head, but it takes time to render the image, send it to the headset, and display it, while the user's head may have minor though constant movement and rotation. The nature of augmented reality makes it more important than usual to solve the issue, as the latency can be disorienting. For example, if the user was looking at a rendered object and steps to the left, the object would appear to be stuck to their head and move left with them for a brief moment, before sliding back where it belongs.

To solve this, the graphics rendering module 322 further implements a depth-based spatial latency compensation system, similar to the asynchronous space warp techniques used in spatial computing. When the workstation renders the 3D images, it also renders a "depth map," or a texture that stores the distance of every pixel in the images to the camera. This is sent to the headset along with the color images. The headset then draws the images on a plane, then uses tessellation to efficiently split the plane into many very small pieces, and slides each piece backwards based on the values from the depth map. This recreates the 3D shape quite closely from the rendered object viewed from the front, but importantly, user can view it from slightly different angles and the object still appears to be shaped correctly. The headset then uses the timestamp of the image to move that plane to where the image was taken, which is where the headset was a few milliseconds prior. Other than some minor disocclusion artifacts, this results in an up-to-date version of the old image from the new angle.

In addition, the graphics rendering module 322 may further compress and decompress the stream of images to minimize the time it takes to send the images from the workstation 210 to the AR headset 20 over the network. Both devices handle the compression/decompression using dedicated hardware to minimize latency. In one embodiment, the hardware acceleration of the Advanced Video Coding, which is also referred to as H.264, is implemented on both the workstation 210 and the AR headset 20.

The software framework 302 further incudes one or more graphics user interface (GUI) to facilitate the user 2 to interact with the software. In the illustrated embodiment, an AR/VR GUI 326 is presented in the virtual scene and interactable via AR/VR headsets 20, AR/VR hand controllers 16&18, user's hand movements, gestures, or user's eye movements. The illustrated embodiment further includes one or more 2D GUIs that are presented on the display devices 12, and interactable via keyboard and mouse 14, or the touchscreen. User interactions via the GUIs may trigger commands which change the state of the application.

The software framework 302 further includes the haptic interface 330 for mediating communication between the user 2 and the computer, monitoring the position, orientation, velocity, and acceleration of the mechanical stylus of the one or more haptic devices 28, and applying force feedback to the user's hands via the one or more haptic devices 28. The haptic interface 330 generates force output directly to simulate a field of force or other mechanical effects such as gravity, friction, damping, or vibration.

The haptic interface 330 sends the input data from one or more haptic devices 28 to the AR/VR GUI 326 and/or the plurality of View Controllers 320. The haptic interface 330 links the one or more haptic devices 28 with the virtual tool that further drives the plurality of View Controllers 320 to interact with the Application State 304 and modifies the system data. The haptic interface 330 may also indirectly interact with the plurality of View Controllers 320 through the AR/VR GUI 326.

In one or more embodiments in which the one or more haptic devices 28 are being used, the graphics and the haptics may be on two separate threads. The haptics and the graphics may have distinct update schedules; for example, haptics at 1000 Hz and graphics at 90 Hz. In this example, the software framework 302 may synchronize the two consecutive graphics updates after approximately every 30 haptic updates, and it is within the skill of artisans to modify the way the haptics and the graphics update and synchronize.

The architecture 300 has been described generally. Further details of the various aspects of the architecture 300 are now provided.

The graphics rendering module 322 may implement a variety of visualizations of the volume or image data either on a 2D plane and/or in a 3D space, including but not limited to a plurality of shaded surface display (SSD) techniques, a plurality of volume rendering techniques (VRT), a plurality of multi-planar reconstruction (MPR) techniques, and a plurality of intensity projection techniques such as the maximum intensity projection (MIP) technique.

In one embodiment, the graphics rendering module 322 may implement the visualization via a plurality of shaded surface display (SSD) techniques which reflect the structures of interests by visualizing the surface representation of a volume layer generated by the volume meshing process. The volume layer is a set of geometry that shares the same rendering material and source. It may be constructed either from an iso-surface contained in a scalar volume dataset, a signed distance field (SDF) of an editable volume object, or a binary volume dataset derived from volume segmentation. Multiple iso-surface layers may be created from the same volume dataset.

The rendering of layers as geometry allows seamless multi-modality rendering. Segmentation or iso-surface layers can be mixed and matched from different scan modalities. The layers from every loaded medical imaging dataset faithfully represent the patient specific anatomy in virtual reality; they can also be accurately superimposed with the actual patient in an augmented or mixed reality environment. As an editable volume object is modified, the associated surface representation may be updated in real-time.

The graphics rendering module 322 may also implement an order-independent transparency (OIT) method which may be used to render an arbitrary unsorted polygons with correctly sorted transparency. This allows displaying the multiple volume layers and other 3D or 2D geometries with adjustable and correct transparency. Applying the OIT method, the opacity of each layer or geometry can be adjusted independently from fully opaque to fully hidden or anywhere in between. In a desired embodiment, the OIT method is implemented using an A-Buffer technique with a per-pixel linked list. As the anatomy is being rendered, the fragments are accumulated in these lists instead of directly composited to a frame buffer. At the end of a frame, the lists are sorted by depth, blended, and then composited with an opaque part of the scene.

It should be appreciated that a plurality of rendering features may be available. At both design time and runtime, the rendering features may be toggled on or off, or have their parameters changed. These features may include, but are not limited to, per-layer colors and transparencies, photo-realistic rendering, diagrammatic cutaways, soft deformation in response to touch, and X-ray visual simulation. In one embodiment, two lighting options may be available: a point light without distance attenuation attached to a camera, and an image-based lighting scheme with directional occlusion. In addition, the meshes may be exported for use in an external software.

The display outputs, from both the 3D and 2D renderings, may be presented on both the AR/VR headsets 20, and the regular computer displays 12 such as monitors, projectors, or televisions. To generate the display outputs on the AR/VR headsets 20, two scene cameras are set to move and rotate based on the positions and orientations of user's head, as well as the Inter Pupillary Distance (IPD) of user's eyes. Stereoscopic vision and depth perception are therefore achieved via the difference of the display outputs for both eyes. On regular computer displays 12, the display output can either be the clone of one of the outputs to the AR/VR headsets 20; optionally, for better experience of the surrounding audiences, the output can be obtained from a separated scene camera which may stay at a fixed point in space, or follow the perspective of the user 2 while keeping the camera movement smooth and steady.

In a desired embodiment, the plurality of volume rendering techniques may include a novel rendering technique referred to herein as a view-ray-ordered volume rendering technique. For visualization of end-user provided volume data, the workflow may be as follows: First, unnecessary structures are eliminated. To do so, the user 2 outlines a 2D region of interest on a maximum intensity projection image of the volume data about any voxel-aligned axis. This 2D region is projected into a 3D polyhedron constrained by the AABB of the one or more volume object, and any information outside of the 3D polyhedron is discarded. Next, a transfer function is specified, aided by an interactive 3D visualization using process 400. The transfer function includes one or more isovalues defining the iso-surface of interest, as selected on a data-value histogram of the one or more volumes. The transfer function furthermore includes scale and bias values that modulate a gradient magnitude driven color ramp. The color ramp tends to distinguish softer versus harder materials. Finally, opacities corresponding to the two extrema of a color ramp may be modified and rendered with exact transparency. All transfer function changes reflect immediately on the 3D rendering. Details are rendered with sub-voxel interpolated details.

The plurality of volume rendering techniques may also include a direct volume ray-caster technique, which renders multiple iso-surfaces, or an SDF obtained from the volume data by marching the ray though the one or more volume object and evaluating intersections with the surfaces. It supports multiple iso-surfaces at different scalar values, with correct transparency, and optionally participating medium rendering. Participating medium rendering simulates increasing opacity as the material gets thicker. Each surface can have different material settings, which may include but not limited to color, opacity, and density for the internal material.

The graphics rendering module 322 may also implement a plurality of MPR techniques to reconstruct a visualization of one or more volume datasets on one or more intersecting 2D planes. The scalar value at each pixel of the plane can be determined by trilinear interpolation of the voxel values of the containing voxel cell in a volume grid. The MPR can be rendered in greyscale or pseudo color with fully configurable mapping of the colors with the voxel values. Transparency can be set along with the color mapping to allow viewing of the 3D rendering behind the MPR overlay, or making certain portion, such as the space outside of the region of interest, less noticeable or even invisible.

The graphics rendering module 322 may also implement a plurality of intensity projection techniques to visualize one or more volume datasets on a 2D plane by projecting all voxels of the volume datasets into a single 2D image. Each pixel of this 2D image is a combination of all projected voxels. According to different methods by which the projected voxels are combined, the plurality of intensity projection techniques may comprise a maximum intensity projection (MIP) technique, a minimum intensity projection technique, an average intensity projection technique, a median intensity projection technique, a standard deviation intensity projection technique, and a cumulative intensity projection technique.

As discussed above, in one or more embodiments in which the one or more haptic devices are being used, the haptic interface 330 may allow interactions between the virtual tool corresponding to the one or more haptic devices 28 and elements within the virtual scene. A haptic proxy is maintained to describe the position of a haptic interface point, which tends to move towards the actual position of the haptic stylus while always staying outside of any haptic-enabled objects. Each object may be assigned with different haptic materials, including but not limited to stiffness, viscosity, static friction, and dynamic friction, as well as a plurality of physical properties such as density, gravity, elasticity, damping, etc. Therefore, the user 2 may perceive a life-like tactile feedback on different surfaces and textures when touching haptic-enabled objects.

In one or more embodiments in which the one or more haptic devices 28 are being used, the haptic interface 330 may track the events of haptic interaction, including the beginning of contact, the end of contact, continuous contact, penetration, to name a few. Custom behavior may be programmed when the events are triggered. The haptic-enabled objects may be configured to be penetrable, and the objects may be penetrated through when the force user applies to the surface of the objects exceeds a predetermined threshold.

In one or more embodiments in which the one or more haptic devices 28 are being used, the haptic interface 330 may implement one or more spatial constraints to the haptic interaction point, which may limit the DOF of the translation and/or rotation of the virtual stylus. The haptic interface 330 may also implement programmable custom haptic force effects, including but not limited to a constant force, a viscosity effect, a vibration effect, or a magnetic effect.

In accordance with the disclosed principles, and in one or more embodiments in which the one or more haptic devices 28 are being used, the architecture 300 may support, via the haptic interface 330, the haptics interaction with volume layers, which may allow the user 2 to touch and interact with one or more volume layers via one or more haptic devices 28. For each volume layer, a subset of voxels near the moving path of the haptic proxy may be collected. An iso-surface within this subset of voxels may be computed and used to determine a new position for the haptic proxy. Multiple iterations of this process may be executed within the frame to refine the proxy position. Based on the offset between haptic proxy and the actual stylus position, as well as all haptic properties applied to the volume layers, an output force may be calculated and applied to the one or more haptic devices 28 as the tactile feedback of the volume layers. The haptics interaction may also work with editable volume objects, whose data and surface representations may be modified in real-time to simulate the change of geometry such as drilling, cutting or augmentation.

In accordance with the disclosed principles, the AR/VR interface 324 may be designed and implemented to provide compatibility with various AR/VR hardware. Specifically, the AR/VR interface 324 may identify AR/VR hardware (i.e., the AR/VR headset 20 and the hand controllers 16, 18) upon startup of the application and may map the correct inputs and outputs for the headset 20 and the hand controllers 16, 18 being used. In a desired embodiment, world-based user interfaces and custom-built hand models may be implemented into the architecture 300 such that each user may receive a consistent experience even though different AR/VR headsets 20 or the hand controllers 16, 18 are being used. The AR/VR interface 324 may support dominant and secondary hand references, allowing the architecture 300 to switch from right-handed mode to left-handed mode at any time. In the disclosed embodiment, the user's hands may track any volume layer or any 3D/2D geometry in the virtual scene via distance tracking. The tracking does not need to be dependent on any collision bounds, allowing more accurate interaction with small objects that are in proximity.

In a desired embodiment, the AR/VR interface 324 includes the AR/VR GUI 326 designed specifically for being used in conjunction with the one or more volume layers and other 3D/2D geometries in accordance with the disclosed principles. Being anchored to the wrist may allow the virtual scene to be scaled up many times its original size and let the user 2 observe the volume layers or geometries from the inside. Icons and tags of the UI buttons may be rendered in a depth-independent manner, allowing the user 2 to see the buttons even when standing inside a solid volume layer. The AR/VR GUI 326 may also be easily moved or hidden to avoid obstructing the view.

As noted above, the Application State 304 may comprise a transform and scene graph system 314 which maintains a data structure that holds the transformational relationships, such as translation, rotation, and scale factors, among all elements in the virtual scene. The data structure may maintain a transformation hierarchy that describes a relation of transformations of scene elements with each-other. The transform and scene graph system 314 may be organized around parent-child relationships via a tree structure with the origin of the global coordinate system being the root and each element in the virtual scene being represented as a node. The position, orientation and scale factor of each node may be defined by the transformation matrix, and the transformation matrix of a parent node is applicable to all its descendant nodes. Multiple tree structure may be simultaneously maintained by the transform and scene graph system 314 to reflect different states of the same set of system data, allowing the user 2 to view any certain state and/or compare between states. In a desired embodiment, multiple scene graphs may be organized to represent the patient anatomy at distinct phases of surgery, such as a preoperative phase, a plurality of the intraoperative phases and a postoperative phase.

The Application State module 304 may also comprise a volume and image data system 316. The volume and image data system 316 receives one or more 3D volume datasets or 2D image datasets generated or maintained by the input data source 332 which may be a medical scanner. Examples of medical scanners that may be used as the input data source 332 for characterizing the physical objects include the computed tomography (CT) scanner, the magnetic resonance imaging (MRI) scanner, the digital radiography (DR) scanner, or the ultrasound scanner, such as those typically used for obtaining the medical images. The input data source 332 may also be a database such as the Picture Archiving and Communication System (PACS), which provides economical storage and convenient access to images from multiple modalities.

The volume and image data system 316 may input the 3D volume data or 2D image data supplied in either a Digital Imaging and Communications (DICOM) format or an MHD/RAW format. The volume or image data with 16-bit and 8-bit integer values may be directly supported; other formats may be automatically converted to 16-bit. To accommodate distinct types of the input data sources, the data contents of scalar 3D volumes (such as CT or MRI scans), or 2D images (such as DR or ultrasound scans), as well as the binary volume or images from the segmentation of the scalar datasets may be processed and maintained by the volume and image data system 316.

The volume and image data system 316 may implement a volume meshing process which generates surface geometries from iso-surfaces across the one or more volume objects while sufficiently performant as to allow constant real-time alterations of the editable volume datasets and their corresponding surfaces. Based on the surface nets algorithm, it may be able to infer and generate a variety of sub-voxel geometric features from a trilinear interpolation function, including the disambiguation of what would otherwise be non-manifold portions of the surface. This is particularly evident in the visualization of a thin or a tunnel-like structure. Surface normal may also be generated for use in lighted rendering, in such a way as to automatically produce an appropriate mixture of hard edges and curved surfaces to satisfyingly represent complex edges without the appearance of undue darkness or obvious facets.

The volume and image data system 316 may also implement a topological smoothing process intended to be used in combination with the volume meshing process, which produces a smoother mesh from the one or more volume object of binary segmentation without overly deviating from the original geometry. Because the topological smoothing process takes place before regular meshing, the smoothed mesh and scalar data are self-consistent, and the system's output is fully and transparently compatible with any volume-manipulating features and can be trivially converted back into the original binary segmentation. The smoothing computation takes place partially on a Graphic Processing Unit (GPU).

The volume and image data system 316 may also implement a series of post processing algorithms of noise reduction to improve the visual fidelity of volume or image visualization. The edge and feature preserving smoothing algorithm may be executed upon the one or more volume or image datasets to suppress low-amplitude noise across all frequencies and make voxels or pixels of the same material cluster closer in a scalar value. Upon the output of the smoothing algorithm, the algorithm of small isolates culling may be executed to remove additional noise by replacing topologically isolated small fragments within the one or more 3D volume datasets or 2D image datasets with smoothed data. Upon the output of the small isolates culling algorithm, a deconvolution algorithm may be executed which simultaneously hardens edges or corners, and smooths where no edge or corner exists. Thus, the influence of a point spread function is removed, voxels or pixels of the same material cluster closer together in the scalar value, and the remaining fragments of noise become more topologically isolated. Upon the output of the deconvolution algorithm, the small isolates culling algorithm may be executed again—thus, topologically isolated small fragments that were not identified in the first execution of the algorithm may be replaced with the smooth data.

According to the disclosed principles, the number of segmented volume objects produced from a same source volume object may optionally be recombined into a single volume object having auxiliary layer ID voxels. A layer ID may be used to simulate a single object consisting of distinct, interconnected materials. In addition to, or alternatively, the segmented volume objects may be cropped to an Axis-Aligned Bounding Box (AABB) containing existent voxels, while retaining position information. In addition, or alternatively, the number of segmented volume objects produced from the same source volume object may be individually cropped to the AABB of the union of their existent voxels. In one embodiment, the segmented volume objects are converted to scalar volume objects via a topological smoothing process.

The volume and image data system 316 may also implement a volume editing process which allows the one or more editable volume objects and the one or more surface representations associated therewith to be modified in real-time or separated into the multiple independent segments. The area being edited may be specified by either the signed distance function (SDF) or a connected component labeling (CCL) process.

The signed distance function (SDF) is a mathematical function that can return the signed distance from the cut boundary to any point in the one or more volume objects. The SDF may include but is not limited to a plane, a geometric primitive which may be a cuboid or a sphere, or a manifold mesh. The editing modifies the original one or more volume objects to reflect the remaining part, and if needed, generates the additional volume objects for the newly cut segments. The region of interest for the editing, which is conservatively defined as any cuboidal area that could contain all voxels being modified, may define the size and dimension of the new volume objects. The voxel values from that area are copied from the original volume data. To construct the cut hollow surface in the original one or more volume objects and the solid surface in the new ones, the signed distance function shall be applied to every voxel in the region of interest in the original one or more volume objects, and then applied in the new one or more volume objects but with the distance sign reversed. The new signed distance value at any voxel shall be the minimum of the original value and the distance returned from the function.

In a desired embodiment, user may define one or more SDFs through auxiliary 3D shapes introduced via user interaction. In another desired embodiment, the volume cutting feature further comprises a paint to separate a mode adapted to define cut regions by gradually painting on one or more editable volume objects by a virtual paint bush of various shapes and dimensions. The area to be separated may be rendered with highlighting visual effects for the user 2 to preview the cut regions before cutting.

The connected component labeling (CCL) is a process which uniquely labels all subsets of the voxels whose represented geometries are connected. The volume editing may be achieved by breaking such connectivity with one or multiple mesh based cutting boundaries defined by the user 2. In an embodiment, the editable volume system may further utilize the CCL process adapted to detect the separation of the one or more volume objects and the surface representation associated therewith. In another embodiment, the CCL process may be adapted to detect whether a cut specified by the user 2 may successfully separate the one or more editable volume objects, and the forecast of the cutting results may be presented to the user 2 before the cut is finalized.

One or multiple new editable volume objects may be generated to describe the newly separated subsets of voxels, with the voxel values copied from the original one or more editable volume objects. To construct the newly cut surfaces resulted from user defined cuts on both the original and new editable volume objects, the values of the voxels in all voxel cells that intersect with the boundary mesh shall be modified according to the minimum distances between the voxels and the cut surfaces.

To update the 3D rendering of the editable volume objects, volume meshing may be re-executed once volume editing is completed. The user 2 may have multiple options to interact with the newly generated volume objects. These interaction features may include removal, maneuver, and various measurements.

The volume and image data system 316 may also implement a volume ray casting process, which may effectively and accurately calculate the first point where a given ray intersects with an iso-surface of a volume dataset, or a signed distance field of an editable volume object. This functionality facilitates other volume operations including ray casting and collision detection.

As noted above, the Application State 304 may also include a view object system 318, which maintains objects in the virtual scene and provides a unified interface to support all core features including but not limited to undo, redo, save, load, and networking. Other application systems useful for application-specific visualizations and user interactions may derive from the view object system 318 to apply the unified interface and features.

As noted above, the plurality of View Controllers 320 may issue commands to create, modify or destroy the system data of different application systems. A plurality of interaction features may be implemented by specific application systems and corresponding view controllers. Said interaction features may comprise one of more of the following: 1) a spatial tracking feature; 2) a user maneuver feature; 3) a volume editing feature; 4) a measurement feature; 5) a snapshot feature; 6) a 3D visualization feature; 7) a 2D visualization and overlay feature; 8) a drawing and annotation feature; 9) a hardware placement feature; 10) an eraser feature; 11) a 3D comparison feature, 12) a co-registration feature, or 13) an AR superimposition feature. Each interaction feature is described below.

The spatial tracking feature may allow high precision tracking of the data in the Application State 304. For any tracking subject, which is typically associated with the AR/VR devices such as the AR/VR hand controllers 16, 18 or the AR/VR headset 20, the distance to any tracked object can be calculated to help the plurality of View Controllers 320 execute the interaction features and specify the one or more elements in the virtual scene being interacted by the user 2. Events can be associated to each tracked object, and they can be automatically triggered if the distance to the tracking subjects meets the predefined criteria.

When a tracking request is made, the distance can be interpreted by plurality of mechanisms, including but not limited to a signed distance function (SDF), a global SDF, or a closest point searching. The SDF is a mathematical function which defines a geometric primitive, or a union of multiple primitives and calculates the distance to it from any given point in a 3D space. It may define or approximate the tracking distance to any virtual scene element based on its transform data maintained by the transform and scene graph system 314. The sign of the distance value may describe whether the tracking subject is inside or outside of the tracked objects. For any volume layer of a volume data, the global SDF can be computed to aid in accurate tracking. The nearest position on the volume layer is estimated using the gradient of the SDF as a direction to project that distance. If the tracking request occurs for the subject outside the volume grid, the nearest point on the boundary of the volume grid is used to locate the nearest position on the surface. For any objects that can be represented or approximated by a collection of points, such as the polygon meshes with dense vertices, the tracking distance can be determined by searching the point closest to the tracking subject and calculating the distance to such point.

In accordance with the disclosed principles, the user maneuver feature may allow the user 2 to intuitively move, rotate, or scale one or more elements in the virtual scene in lifelike ways. This feature may allow the user 2 to observe the one or more 3D geometries such as the volume layers from the outside or from inside out. Using triggers or buttons on the hand controllers 16, 18 as well as the position and the orientation of the hands obtained from the AR/VR interface 324, the corresponding View Controller 320 may generate commands to modify the translation, orientation and/or scale factor data maintained by the transform and scene graph system 314 to update the transform of one or more objects being maneuvered.

In one or more desired embodiments, when user 2 grabs with one hand by squeezing a trigger on the hand controller 16 or 18, one or more objects being maneuvered may be freely moved and rotated; when user 2 uses both hands to grab at empty space outside the objects, the objects may rotate and scale around their own geometric centers; when both hands grab inside an object, said object may be pivoted to user's both hands, and moved, rotated, and/or scaled with regards to the hand movement.

In one or more desired embodiments, the degree of freedom (DOF) of the maneuver may be constrained so the translation along one or more axes, and/or the rotation around one or more axes may be restricted to a limited range of motion, or even completely disabled. The user 2 may also define the rotational pivot. A set of gizmos may be present with the virtual scene elements to aid such maneuver with constrained DOF.

In accordance with the disclosed principles, the volume editing feature may allow the user 2 to modify one or more editable volume objects in real-time. The volume editing feature may implement a volume cutting tool, which allows the user 2 to cut the one or more editable volume objects and the surface representations associated therewith in user defined regions. When the user 2 confirms the cuts, the editable volume objects are then modified so the corresponding surface representation matches the cuts, and the additional volume objects may be generated to represent the newly cut partitions. The volume editing feature may also implement a paint-to-segment tool which allows the user 2 to define cut regions by gradually painting on the one or more volume objects by a virtual paint brush of various shapes and dimensions. The volume editing feature may also implement a volume sculpting tool which allows the user 2 to frequently modify the one or more volume objects and the surface representation associated therewith in the region specified by the user 2, to gradually remove materials from the represented geometry or add materials to it.

The measurement feature may provide accurate 3D and 2D measurements of a plurality of spatial properties based on the source dataset. An application system for the measurement feature may be implemented within the Application State 304 to maintain and control the data that describes all measurement elements. The measurements may be one of more of the following: 1) the distance between two points, 2) the cumulative length of a polygonal chain, 3) the angle between two lines, 4) the angle between two planes, 5) the circumference of a circle, 6) the volumetric size of a user defined space, and/or 7) the volumetric size within an iso-surface. The measurements feature may further utilize a surface binding process to attach measurement points onto a surface of any volume layer or other 3D geometry close by, or onto a plane that display 2D images or renderings. As can be appreciated, this may increase the accuracy of the point placement, thus increasing measurement accuracy. When the user 2 maneuvers scene elements, the attached measurement points may be moved altogether, and the measurement results may be updated in real-time.

The snapshots feature may allow the user 2 to capture one or more pictures or videos of the virtual scene from any user specified perspective at any user defined time. One embodiment may allow the snapshot pictures to be saved as "PNG" files, and the snapshot videos to be saved as "MP4" files. The user 2 may look through a virtual viewfinder to help focus on the virtual objects to be captured. Once a snapshot is taken, a preview may be displayed on the AR/VR GUI 326, and the image may be saved under a designated path. The user 2 may switch between portrait and landscape modes as desired. Once the snapshots are saved, they may be reviewed by the user 2 on the AR/VR GUI 326, and the saved files may be accessed by the user 2 later.

The 3D visualization feature may provide real-time configurations of the visual properties of one or more 3D objects, which may be volume datasets or 3D geometries. These visual properties include but not limited to colors, level of transparency, isovalues, transfer functions, special visual effects achieved by shaders, etc. An application system may be implemented within the Application State 304 to maintain, and control said visual properties. A graphics rendering module 322 may update the rendering of the one or more 3D objects in real-time to reflect the changes of the visual configuration.

The 2D visualization and overlay feature may present a 2D visualization of one or more 3D volume datasets or 2D image datasets in the virtual scene. A plurality of 2D rendering techniques, such as the multi-planar reconstruction (MPR) techniques, or the intensity projection techniques may be applied to visualize one or more volume datasets in 2D. In a desired embodiment wherein one or more 2D image datasets exist, the rendering of 2D dataset may also be presented. The rendering of multiple datasets may also be combined by an image fusion technique. The 2D visualization may be presented on an AR/VR GUI 326, a 2D GUI 328, or one or more 2D planes across the 3D visualization of the one or more volume datasets in the virtual scene. The planes may be the axial, sagittal, or coronal planes of the 3D volume, or they may be in any arbitrary orientation. Optionally, the 3D visualization of the volume datasets on either side of any plane may be culled out to better present both the internal structure of the volume datasets and the 2D rendering overlaid on the planes. The graphics rendering module 322 may update both the 3D visualization and the 2D rendering overlay in real-time based on the user interaction. A specific application system may be implemented within the Application State 304 to maintain the data essential to the 2D visualization and overlay feature.

The drawing and annotation feature may allow the user 2 to draw or mark annotations in the virtual scene. One or more annotations, which may be points, lines, curves, symbols and/or texts may be created via a drawing and annotation tool controlled by the AR/VR hand controller 16, 18. An application system for drawing and annotation may be implemented within the Application State 304 to maintain and control said annotations. In a desired embodiment, the annotations may be applied on the surface of one or more 3D geometries such as volume layers or 3D geometries and moved along with the associated 3D objects. In a desired embodiment wherein one or more 2D rendering planes exist, the drawing and annotations may be applied on the 2D planes. The drawing feature may also include an option to measure the accumulated length of the lines or curves. Visual properties such as the color, the line width and the dash style may be configurable through the AR/VR GUI 326.

In a desired embodiment, a dynamic annotation, which may behave like a laser pointer, may be created, and controlled by the user 2 to point out specific positions and features on the one or more virtual scene elements for the benefit of the viewing audience. The point where the laser encounters the one or more surfaces or volume layers may be calculated by a ray casting technique, and the point may be visually highlighted to help draw attention to the point of interest. In a desired embodiment wherein, multiple users participate in a real-time interactive session via networking, the movement of the dynamic annotations may be synchronized with all users over the network through commands exchanged via the networking module 310.

The hardware placement feature may introduce one or more of the 3D models to the Application State 304. These 3D objects can be independently included in the virtual scene or mounted to an existing element in the scene. In a desired embodiment wherein, the application is implemented for one or more of surgical planning, patient engagement and/or medical education, the hardware objects may be models of medical implants, surgical plates, screws, or surgical instruments. An application system for hardware placement may be implemented within the Application State 304 to maintain and control the hardware models. In the transform and scene graph system 314 the hardware may be attached to any element in the scene.

In a desired embodiment wherein one or more 2D rendering planes exist, one or more projected contours or cross sections of one or more hardware models may be generated and superimposed on the 2D renderings of the volume or image datasets on the planes. The projected contours or cross sections may reflect the real-time position and orientation of the hardware models with respect to the 3D volumes or 2D images visualized on the corresponding 2D rendering planes. When the user 2 maneuvers one or more hardware models in the 3D space, the projected contours or the cross sections may be updated simultaneously. When the user 2 maneuvers one or more projected contours or the cross sections on 2D planes, the same movement may be applied to corresponding hardware models in real-time.

In a desired embodiment, the hardware models such as surgical plates may be bent against the surface of one or more volume layers, fitting the curvature of the anatomy structure. In another desired embodiment wherein the hardware models overlap with other 3D objects, the level of overlapping may be measured, and may be visualized by a color gradient on the surface of the objects representing the depth of intersection.

The eraser feature may allow the user 2 to erase one of more elements from the virtual scene. The eraser may be controlled by user's hand movement via the AR/VR interface 324, and the tracking feature may monitor its distance to all erasable objects in the virtual scene. When the user 2 moves the eraser onto one or more erasable objects, a specific View Controller 320 of the eraser feature may issue a command to destroy the system data corresponding to said objects, which then triggers the removal of the objects from the view.

The 3D comparison feature may allow the user 2 to view and compare one or multiple sets of 3D objects. In one embodiment, the visualization of multiple sets of volume datasets, which may be the digital twins of the patient anatomy at different surgical phases, may be placed side by side for direct comparison. In another embodiment, the visualization of multiple volume dataset may overlay with each other for better comparisons. In another embodiment, the one or more volume objects may superimpose with their own mirrored inversion, highlighting the symmetric differences.

The co-registration feature may aid in aligning (co-registering) multiple elements, such as 3D volume datasets, 2D image datasets, and 3D geometries. The datasets may be of different modalities. The co-registration represents pairwise proper rigid transforms between the coordinate spaces of the elements. The 3D volumes may be visualized by either 2D multi-planar reconstruction (MPR) on axial/sagittal/coronal planes or overlaid maximum intensity projections (MIP). The co-registration may be performed manually via the mouse and keyboard controls, or semi-automatically via a partial Procrustes superimposition of plurality sets of user designated feature points with each set specifying the same feature on different elements. A resulting transformation matrix may be computed to describe the co-registration and said transformation matrix may be applied in the transform and scene graph system 314 to align these elements in the virtual scene.

The AR superimposition feature may superimpose the visualization of the virtual scene with real-world objects and maintain constant relative rotations and translations. The user 2 or equivalently any trained professional may register one or more 3D volumes, 2D images, or 3D geometries with virtual 3D objects that represent the optical marker objects 36 in the virtual scene. The optical marker objects 36 may be attached to one or more real-world objects of significance in the same way that their digital twins are registered with the virtual scene. When an AR headset, or a VR headset with camera passthrough is in use, a plurality of optical tracking techniques may be used to detect the 3D position and orientation of the physical markers in real time, allowing their virtual counterparts to overlay with them. Following the transformational matrix maintained in the transform and scene graph system 314, the rest of the virtual scene may be correctly superimposed with real-world counterparts when displayed through the AR/VR headset 20. When one or more real-world objects with fiducial markers are moved, all corresponding virtual objects may move automatically to maintain the superimposition. In a desired embodiment, the objects registered with the fiducial markers may be surgical instruments, or the body of a patient; the fiducial markers may be one or more blocks with QR code, or one or more sets of 3D optical markers.

In a desired embodiment, one or more real-world objects, which may be anatomy structures inside of a patient body, may be partially or fully invisible due to obstructions by other objects on the outside, and the AR superimposition feature may help reveal such internal objects by visualizing the superimposed virtual counterparts. In another desired embodiment, the superimposed virtual objects may represent a state different from the real-world objects, for instance, the preoperative anatomy vs. the surgical planning; such AR superimposition may highlight the differences between multiple states and guide any actions that need to be performed, which may be surgical procedures.

In an example, the user 2, who may be a doctor, may want to view the 3D reconstructions of the head of a patient and conduct surgical planning using the workstation 10, 110. The doctor may use the workstation 10, 110 and may be wearing the AR headset 20 for viewing the 3D and 2D visualizations of the medical scans of the brain. The doctor may import the 3D medical scans as the cranial CT or MRI, the 2D medical scans such as DR, the segmentation of the medical scans and/or 3D geometries representing patient anatomy into the Application State 304 via the input data source 332. The entirety of the Application State 304 may also be previously saved in one or more files, which may be loaded on the workstation 10, 110 and viewed using the AR/VR headset 20.

The AR/VR interface 324 may update the doctor's hand position, the doctor's head position and orientation data from the AR/VR hardware (i.e., the AR/VR headset 20 and the hand controllers 16, 18) to the AR/VR GUI 326 or the plurality of view controllers 320. The plurality of view controllers 320 may issue one or more commands for creating, modifying, or destroying the data to the state change router 312. In turn, the state change router 312 may further route the commands to the Application State 304, the undo/redo module 308 and/or the networking module 310. When said commands are received by the Application State 304, the system data corresponding to one or more application systems may be created, modified, or destroyed; when said commands are received by the undo/redo module 308, they may be maintained in the undo/redo stack for future undo/redo operations, which may reverse previously executed commands; when said commands are received by the networking module 310, the commands may be sent to and synchronized with other users on the network. Through the execution of commands, the doctor may interact with the virtual representation of the patient head and use all available features in the application to explore the patient anatomy, conduct the surgical planning, perform the patient consultation, or assist the surgery.

The graphics rendering module 322 may render the 3D and 2D scans of the head anatomy in 3D space or on one or more 2D planes via the plurality of graphics rendering mechanisms. The graphics rendering module 322 may properly render both left and right views according to the position and orientation of the doctor's head. The images of the brain may be presented on the display screen 12 and the AR/VR headset 20.

Figure 5:
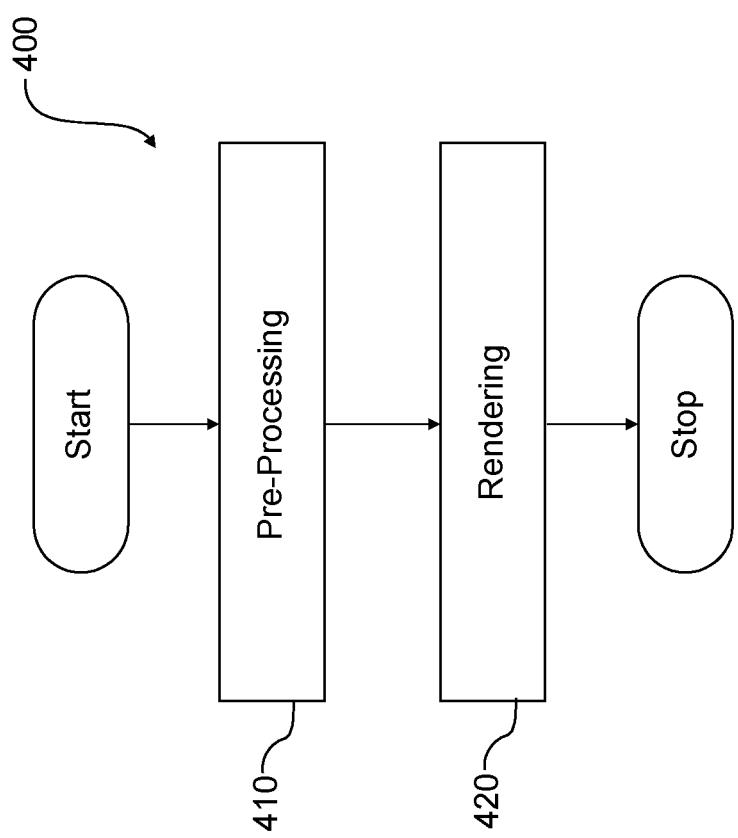
FIG. 5 illustrates a process according to a disclosed embodiment.

When AR superimposition is configured, the AR/VR headset 20 may augment anatomical structures of the patient head with the visualization of its digital twin. On the display of the AV/VR headset, the original image and models may be superimposed onto corresponding anatomical structures of the actual patient to reveal internal anatomy structures that are not visible from the outside; the results of surgical planning may also be superimposed onto the actual patient to help guide the surgical procedures. Virtual models and scans may move and orient correctly when the corresponding actual anatomy is viewed from different angles and positions. FIG. 5 illustrates a process 400 according to a disclosed embodiment. As discussed above, the process 400 is the view-ray-ordered volume rendering technique for the GPU. It is well known that volume rendering is a computationally expensive operation. The medical images can contain hundreds of millions of voxels. Thus, it may be desirable to restrict rendering to only the interesting voxels; however, even one iso-surface of interest within the medical image may easily include tens of millions of voxels. Furthermore, for many applications, it may not be sufficient to render the outermost visible surface of the object embedded in a volume. Numerous transparent elements may be visible throughout the volume. This may prohibit a simple Z-buffering technique.

At the same time, the expectations of display resolutions and frame rate are climbing, which further exacerbate the difficulties of the volume rendering. Typical volume rendering techniques support interactive rates of approximately 10 Hz, usually restricted to a small viewport in a desktop application. On the other hand, modern users demand virtual and or augmented reality experiences, which may run at the frame rate of up to 90 Hz with render resolutions upwards of 5 million pixels. The render resolution required for the virtual or augmented reality rendering climbs higher every year. Under these circumstances, volume rendering may present an extreme computational burden that may only be met by the graphics processing unit (GPU).

Generally, volume rendering may be classified as an image-order technique or an object-order technique. The Image-order technique traces the ray or a cone through the volume for every pixel on the imaging plane. This is described e.g., in Hanspeter Pfister, "Hardware-Accelerated Volume Rendering", *Visualization Handbook*, 2(3), pp. 229-258, Elsevier, 2005 (hereinafter "Hanspeter Pfister"). While many techniques for accelerating these ray-traces exist, a volume ray-tracing scales poorly with increasing resolution. Small stepping of the rays leads to good locality of the reference, but the exhaustive sampling of the volume across too many pixels is inefficient. Large stepping of the rays via an empty-space-skipping technique alleviates the burden of sampling, but introduces locality of reference problems, which also results in inefficiency (particularly for complex volumes). The Image-order techniques predominate due to their simplicity of implementation, but they do not suit real-time, high-resolution applications.

The object-order techniques, on the other hand, draw the volume elements onto the imaging plane. One technique is known as a volume slicing technique, whereby the volume is rendered via an ordered stack of textured quads. This is also described in Hanspeter Pfister. While possessing some advantages, such as high locality of reference and good utilization of hardware interpolation, the volume slicing is an exhaustive sampling of every voxel in the volume. Thus, it only scales to small volumes. Furthermore, slicing exhibits serious rendering artifacts.

The other major object-order technique is a volume splatting technique, whereby each voxel is independently drawn onto the imaging plane. Described in Hanspeter Pfister. A central consideration of the splatting is how to draw the voxels in order, so that they composite together correctly. Existing techniques include an exhaustive Painter's Algorithm rendering technique from a dense 3D array, as described e.g., in G. Frieder, D. Gordon and R. A. Reynolds, "Back-to-Front Display of Voxel Based Objects", in *IEEE Computer Graphics and Applications*, vol. 5, no. 1, pp. 52-60, January 1985; pre-sorting for one or more view directions on the CPU, as described e.g., in F. Vega-Higuera, P. Hastreiter, R. Fahlbusch and G. Greiner, "High performance volume splatting for visualization of neurovascular data", VIS 05. *IEEE Visualization*, 2005, 2005, pp. 271-278; or Inigo Quilez, "Volumetric Sort", (https://iquilezles.org/articles/volumesort/) (hereinafter "Volumetric Sort"); or extracting a voxel order from a multidirectional run-length encoding format as described e.g., in J. Orchard and T. Möller, "Accelerated Splatting using a 3D Adjacency Data Structure", *Proceedings—Graphics Interface*, 2001, 2001, pp. 191-200. All existing techniques are fundamentally sequential and CPU-bound.

Unlike the image-order and the object-order techniques, and unique solely to the process 400 disclosed herein, is the way the GPU is used to draw the voxels in view order, from a compressed representation of the voxel coordinates. The coordinate compression keeps memory consumption and bandwidth usage low. High locality of the reference is maintained through all stages of the algorithm.

As will be discussed below in more detail, the process 400 comprises a pre-processing stage 410 followed by a rendering stage 420. In the pre-processing stage 410, each voxel possibly existent within the coordinate range of the one or more volume objects must undergo a binary classification as existent or nonexistent; i.e., to be rendered or not rendered, respectively. The details of this classification are application-dependent and not essential to practice the principles disclosed herein. However, the process 400 performs an amount of work proportional to the number of the existent voxels (until the final rasterization stage). Thus, the process 400 requires the binary classification as an input. The classification is either created as, or transformed to, a binary mask volume.

In one embodiment, the binary mask volume is transformed into a Histogram Pyramid such as one described e.g., in G. Ziegler, C. Theobalt, and H. P. Seidel, "On-the-fly Point Clouds through Histogram Pyramids." 11*th International Fall Workshop on Vision, Modeling and Visualization*. Vol. 2006, pp. 137-144. Amsterdam, The Netherlands: IOS Press, 2006. In the disclosed embodiment, the Histogram Pyramid is a hierarchical grid of element counts per grid cell. The original binary mask volume is retained to comprise the leaves of the Histogram Pyramid.

Each existent voxel may be logically assigned an index according to some fixed and particular (but arbitrary) traversal order of the Histogram Pyramid, henceforth a "fixed order." Voxel indices range from 0 to the number of existent voxels.

A look-up table may be created that maps high-order bits of the voxel coordinates to high-order bits of voxels 'fixed order' (i.e., via a prefix sum). Exactly how many bits are mapped is an implementation detail that is not essential to practice the principles disclosed herein. In any case, the binary mask volume and the look-up table may be constructed such that they are sufficient to transform any existent voxel's coordinates to its fixed order index.

As used herein, the voxel data may comprise any desired attributes for rendering each voxel, such as e.g., color, opacity, emittance, scalar magnitude, or partial derivatives of gradients. For each existent voxel, the voxel data may be stored in the fixed order. Depending on the application, the 1D fixed order may be mapped to the GPU storage directly via a buffer, or to elements in a 2D or 3D texture using a space-filling curve. In addition to, or alternatively, the voxel attributes themselves may be compressed in the 2D texture.

In the rendering stage 420, the voxels may be rasterized in order of distance from the camera. The rasterization feature of the graphics processor may be exploited. According to the disclosed principles, and without loss of generality, front-to-back compositing with front-to-back view order may be implemented herein. The rendering stage is generally described as follows.

Indirect drawing may be enabled on the graphics processor. The number of vertices to draw may be supplied as the number of existent voxels. The vertex ID provided to the vertex program is interpreted as a voxel draw sequence number. Using one Histogram Pyramid traversal per vertex shader invocation, the voxel draw sequence numbers may be transformed to 3D coordinates of the existent voxels as sorted in view order. The sorted voxels may be rasterized immediately by the graphics pipeline and then discarded. Because graphics hardware guarantees correct ordered blending of the primitives according to their order of submission, this process may be sufficient for correct rendering in view order.

Figure 6:
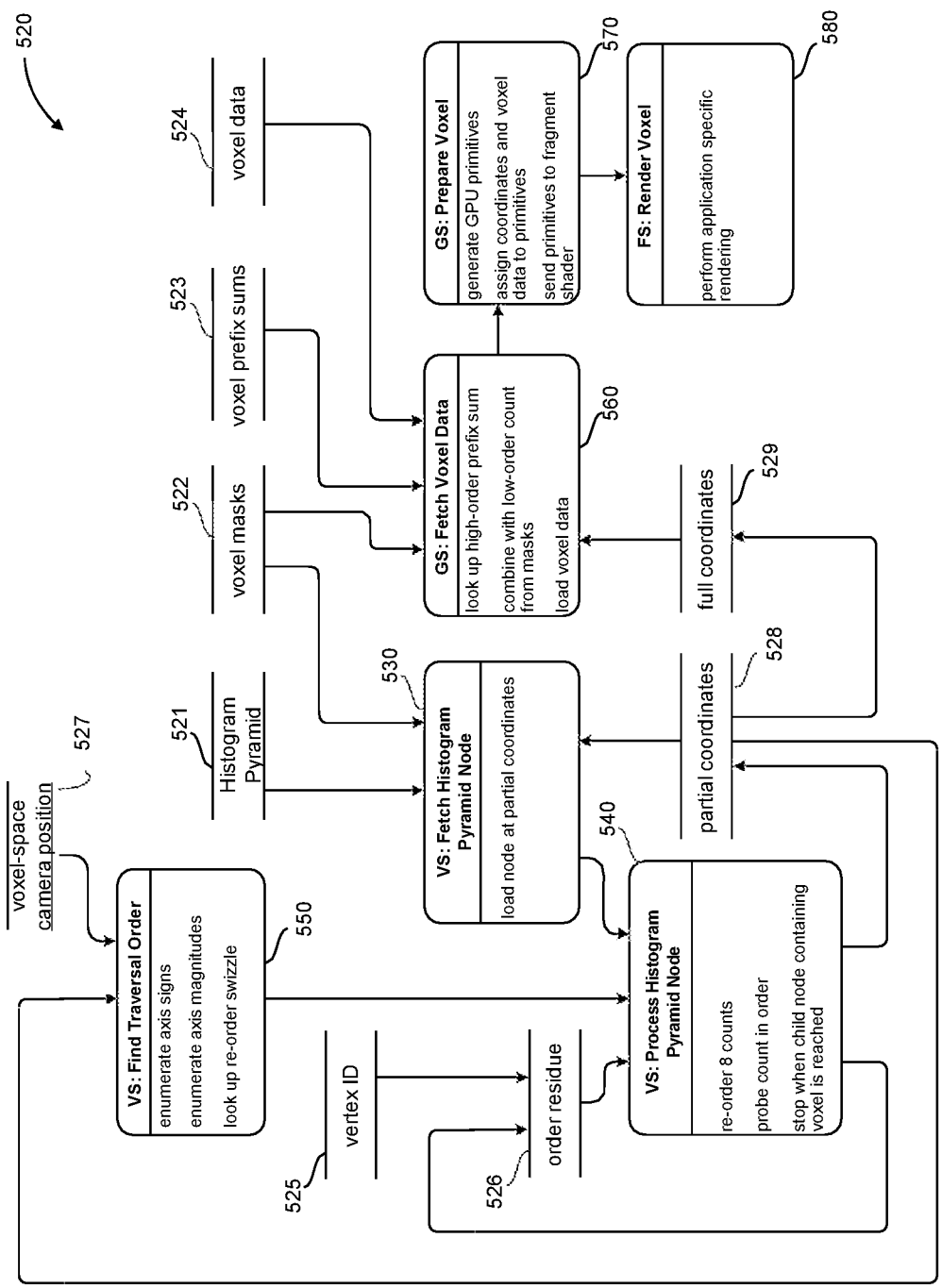
FIG. 6 illustrates details of a rendering stage used in the process illustrated in FIG. 5.

The rendering stage 420 may be implemented via a vertex shader (VS), a geometry shader (GS), and a fragment shader (FS). Details of the rendering stage 420 now follow with respect to FIG. 6. Specifically, FIG. 6 illustrates details of the rendering stage 420 that may be used in the process 400 illustrated in FIG. 5. The rendering stage is shown having six functional blocks 530, 540, 550, 560, 570, 580. The blocks 530, 540 and 550 may be implemented by the VS, the blocks 560 and 570 may be implemented by the GS, and the block 580 may be implemented by the FS. Inputs 521, 522, 523, 524, 525, 526, 527, 528 and 529 into the functional blocks 530, 540, 550, 560, 570, 580 are also shown in FIG. 6.

In the illustrated embodiment, the VS implements block 530 to fetch the Histogram Pyramid node, the block 540 to process the Histogram Pyramid node and the block 550 to find the traversal order; the GS implements the block 560 to fetch the voxel data and the block 570 to prepare the voxel for rendering; and the FS implements the block 580 to render the voxel. This functionality is now described.

The VS may fetch the Histogram Pyramid node (block 530) using the Histogram Pyramid input 521 and the voxel mask input 522. At the block 530, the node may be loaded at a partial coordinates input from the partial coordinates input 528. The loaded node at the partial coordinates may be input into the block 540. The block 540 may also input the output of the block 550 (traversal order) and an order residue from the order residue input 526. In the block 540, the VS, may re-order the eight counts of the node, probes each count in order, and may stop when the child node containing the voxel is reached. In block 550, the VS may enumerate axis signs and magnitudes and look up a re-order swizzle using inputs such as the voxel-space camera position 527 and the partial coordinates 528.

For any view ray, exactly forty-eight traversal orders are possible per Histogram Pyramid node, due to the grid structure of the Histogram Pyramid. These orders may correspond to permutations of six axis orders multiplied by eight axis signs as described e.g., in Volumetric Sort. For each step of the Histogram Pyramid traversal (block 540), a traversal order may be determined (block 550) and used to rearrange the eight Histogram Pyramid node counts into an order of increasing distance with respect to the view ray. The linearized counts may then be probed until the ancestor node of the current voxel is found (block 540).

To determine the Histogram Pyramid node traversal order (block 550), the voxel-space camera position 527 may be subtracted from the bounding box center of the voxel-space Histogram Pyramid node. The resultant vector may be normalized. The signs and relative magnitudes of the normalized view vector's three components may be transformed into a discrete traversal order between 0 and 47.

For an orthographic projection, all the view-rays are identical with respect to all the Histogram Pyramid nodes. Only the voxel-space imaging plane normal may be needed to determine the traversal order, and this is constant per invocation of the VS. Therefore, upon every access to the Histogram Pyramid node, the node may be re-ordered in a constant manner. Such constant re-ordering may be achieved via a pre-compiled shader variant per traversal order, with the correct one selected just prior to the rendering.

The voxel coordinates 529 may be passed from the VS to the GS and used at the block 560 to fetch the voxel data. The block 560 inputs the voxel masks 522, the voxel prefix sums 523 and the voxel data 524 and may perform the following functions: looks up the high-order prefix sum, combines it with the low-order count from the masks and loads the appropriate voxel data. The output of the functional block 560 is input into the block 570, which may prepare the voxel for the rendering. To do so, the block 570 may generate the GPU primitives, assigns coordinates and the voxel data to the primitives, and send the primitives to the FS.

To perform these functions, the fixed-order voxel index may be obtained via the sum of the value from the look-up table at the high-order bits of the voxel coordinates with a Hamming weight of the preceding voxel existence bits from the low-order binary mask obtained during the Histogram Pyramid traversal. The voxel data may then be fetched using the fixed-order index.

The FS performs the block 580, which is the rendering of the voxel. To do so, the FS may perform an application-specific rendering. For example, in one application, the voxel data may include scalar values for each of eight corners, and a volume rendering integral may be evaluated along the view ray passing through the fragment and the voxel. Correct ordered transparent composition may guaranteed based on the disclosed principles.

As discussed above, the execution of the rendering stage 420 may be split between the VS, GS, and FS. This may be done, in part, because it is necessary to access required GPU hardware functionality, such as primitive generation, throughout the stage 420. This splitting may also suit the GPU's internal load-balancing mechanisms. The GPUs may be deeply pipelined and allow numerous VS, GS and FS invocations all running simultaneously.

In implementation, a plurality of tasks may be placed in a different type of shader. For example, the GS may perform the Histogram Pyramid traversal. This would not fundamentally alter the rendering stage 420. The described process 400 may use the voxels as the parallel primitive for both the voxel order determination and the drawing. The existing splatting algorithms may use the voxels as the primitive only for parallel or sequential drawing. The disclosed principles, however, may allow broad data parallelism, highly coherent branches, and high data locality between nearby shader processing units. Furthermore, all data structures employed may be simple and compact enough to be fully re-generated at interactive rates.

Figure 7:
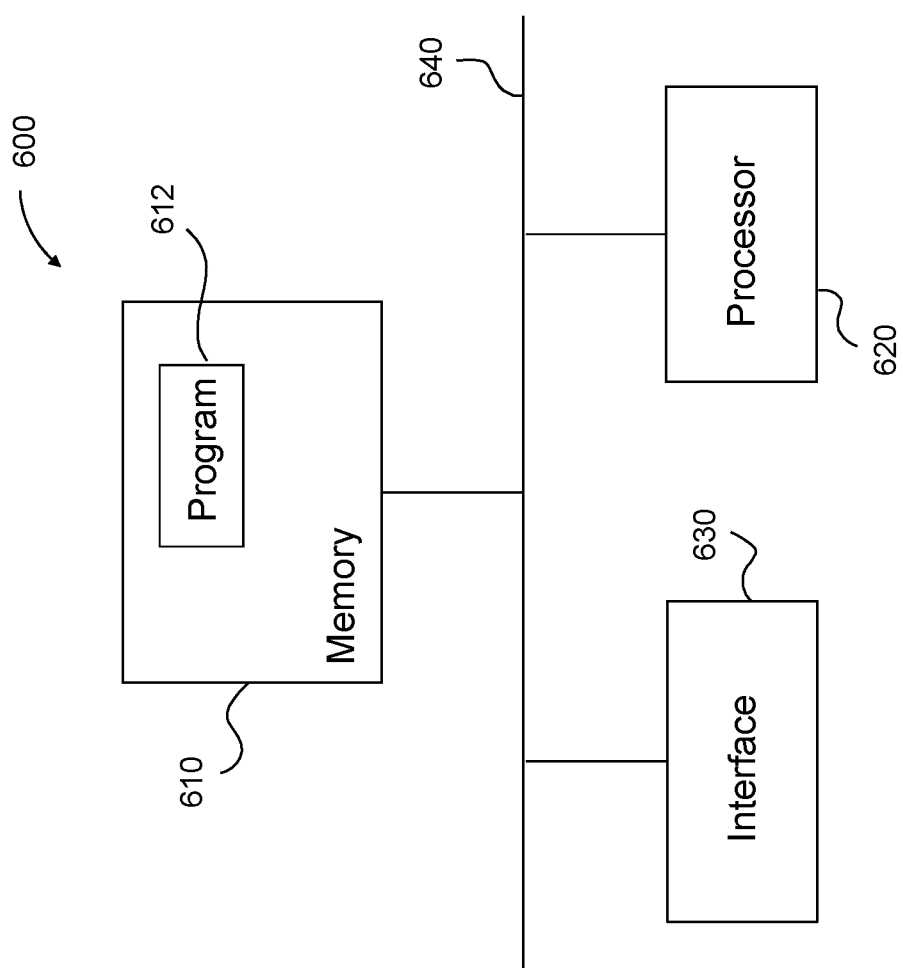
FIG. 7 illustrates an example configuration of a computer or computing device suitable for use in the workstations illustrated in FIGS. 1, 2 and 3.

FIG. 7 illustrates certain components of a computing device 600 that may be utilized in the workstations 10, 110 to execute or that may embody components of the disclosed embodiments. For example, the computing device 600 may include a memory 610, program instructions 612, one or more processors (e.g., processor and a graphics processor) 620 to execute the instructions 612, one or more interfaces 630 (e.g., AR/VR interface 324) connected via one or more buses 640. The memory 610 may be or include one or more of cache, RAM, ROM, SRAM, DRAM, RDRAM, EEPROM and other types of volatile or non-volatile memory capable of storing data. The one or more processors 620 may be or include multiple processors, a single threaded processor, a multi-threaded processor, a multi-core processor, or other type of processor capable of processing data. It should be noted that one or more components of the computing device 600 may be located remotely and accessed via network. Accordingly, the system configuration provided in FIG. 7 is provided to illustrate how embodiments may be configured and implemented.

Method embodiments or certain steps thereof, some of which may be loaded on certain system components, computers, or servers, and others of which may be loaded and executed on other system components, computers or servers, may also be embodied in, or readable from, a non-transitory, tangible medium or a computer-readable medium or a carrier, e.g., one or more of the fixed and/or removable data storage data devices and/or data communications devices connected to the computer. The carriers may be, for example, a magnetic storage medium, an optical storage medium and a magneto-optical storage medium. Examples of the carriers include, but are not limited to, a floppy diskette, a memory stick or a flash drive, a CD-R, a CD-RW, a CD-ROM, a DVD-R, a DVD-RW, or other carrier now known or later developed capable of storing data. The processor 620 performs steps or executes the program instructions 612 within the memory 610 and/or embodied on the carrier to implement method embodiments.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, which are intended to particularly point out and distinctly claim the claimed subject matter.

What is claimed is:

1. A system comprising:
 a workstation for multidimensional data visualization and interaction in an augmented reality (AR), virtual reality (VR), or mixed reality (MR) environment, said workstation comprising at least one of:
  an application state module adapted to:
   maintain a plurality of virtual scenes which describe distinct states of the application and include data and contents presented in AR/VR/MR,
   manage a plurality of application systems and corresponding system data, and
   allow querying and interaction with said application systems and the corresponding system data;
  the plurality of application systems adapted to create, read, modify, or destroy the corresponding system data and execute relevant application commands;
  the plurality of system data comprising at least one of:
   multidimensional data, including three-dimensional (3D) volume data, or two-dimensional (2D) image data,
   3D or 2D geometry data,
   user input data, including hand position and orientation data, head position and orientation data, or controller input data,
   user interaction data, and
   informational data;
  a save/load module adapted to save the plurality of system data from memory to files, and load the plurality of system data from the files into the memory;
  an undo/redo module adapted to undo or redo user operations;
  a networking module adapted to support multi-user collaboration over the network;
  a state change router adapted to:
   receive a command to create, modify, or destroy the corresponding system data, and
   send the received command to the application state module, the undo/redo module, or the networking module for creating, modifying, or destroying the corresponding system data;
  a plurality of view controllers adapted to:
   query a public interface of the application state for the state of one or more application systems,
   subscribe to events that will trigger if at least a portion of the plurality of system data changes, and
   issue the commands to create, modify, or destroy the system data based on user instruction with plurality of interaction features;
  an AR/VR interface adapted to update the user input data from one or more AR/VR devices to at least one of: an AR/VR graphical user interface (GUI), or a plurality of view controllers; and
  a graphics rendering module adapted to:
   receive the system data from the plurality of view controllers,
   visualize the data on at least one of: 2D space or 3D space via a plurality of graphics rendering mechanisms, and
   display the visualizations on at least one of: a display device, or a GUI;
 one or more AR/VR devices for stereographically displaying a view of the application state and visualizing the system data associated therewith, wherein the viewpoint is consistent with the physical position and orientation of the AR/VR devices; and
 an AR overlay system adapted to allow the user to view 3D images overlaid over the real world.

2. The system of claim 1, said AR overlay system comprising at least one of:
 an optical tracking module adapted to report the positions and orientations of a plurality of real-world objects of significance by tracking the real-time location of a plurality of optical marker objects attached to the plurality of real-world objects of significance;

an offset compensation module adapted to compute the position of the real-world object of significance based on the position of the marker objects and the shape of the custom attachment; and an overlay rendering module adapted to draw each rendered object in the correct location from the view perspective of the user and superimpose the stereoscopic visualization of the 3D objects or 2D images to their real-world counterparts.

3. The system of claim 2, wherein the plurality of real-world objects of significance includes at least one of: a patient body, a patient anatomy, a surgical instrument, a user interaction device, or an AR device.

4. The system of claim 2, wherein the plurality of optical marker objects includes at least one of: a constellation of spheres or other geometric primitives, a 2D bar code such as a QR Code, a constellation of 2D bar codes, a 2D image, or a 3D object.

5. The system of claim 1, further comprising a haptic interface adapted to interface with one or more haptic devices and implement at least one of:

updating a position, an orientation, a velocity, or an acceleration of the one or more haptic devices to one or more virtual tools in the virtual scene; and applying force feedback to the one or more haptic devices based on user interactions with the one or more virtual tools.

6. The system of claim 1, wherein the multidimensional data comprises 3D or 2D medical imaging of a plurality of modalities, wherein the plurality of modalities includes at least one of: a Computer Tomography (CT) technique, a CT Angiography (CTA) technique, a Cone Beam CT (CBCT) technique, a Magnetic Resonance Imaging (MRI) technique, a MR Angiography (MRA) technique, a Digital Radiography (DR) technique, and an Ultrasonography technique.

7. The system of claim 1, wherein the plurality of application systems comprises at least one of:

a transform and scene graph system adapted to manage a data structure which maintains at least one of:
  a position, orientation, or scale factor of scene elements, including the 3D volumes, the 2D images, the 3D/2D geometries, or results of user interactions, and
  a transformation hierarchy that describes a relation of transformations of scene elements with each other;

a volume and image data system adapted to:
  receive the 3D volume data or the 2D image data from an input data source,
  maintain and process the 3D volume data or the 2D image data,
  generate one or more geometries to represent the surfaces derived from the 3D volume data or the 2D image data,
  generate or modify one or more editable volume objects in real-time,
  separate one or more editable volume objects into multiple independent segments, and
  update surface representation of one or more editable volume objects;

a view object system adapted to maintain objects in the virtual scene and provide a unified interface to support at least one of: undo, redo, save, load, and networking; and a plurality of other application systems adapted to define application-specific features and user interactions.

8. The system of claim 7, wherein the volume and image data system further comprises a volume-surface conversion process adapted to:

generate one or more surface representations from the 3D volume data; and construct the 3D volume data based on the one or more 3D geometries.

9. The system of claim 1, wherein the graphics rendering module further comprises a remote rendering system adapted to provide images of greater 3D resolution and visual fidelity than typically possible with standalone AR/VR headsets with have limited computational power onboard, by rendering the images by the computer workstation based on the position of the AR/VR headset and send the images to the headset to draw in front of the user's eyes.

10. The system of claim 9, wherein the remote rendering system further comprises a depth-based spatial latency compensation system adapted to compensate the latency between a user performing an action and having the action represented in the images.

11. The system of claim 9, wherein the remote rendering system further comprises an image compression and decompression system adapted to minimize the time taken to send the images between the computer workstation and the AR/VR headsets over the network.

* * * * *